United States Patent [19]
Kang et al.

[11] 3,960,832
[45] June 1, 1976

[54] POLYSACCHARIDE AND BACTERIAL FERMENTATION PROCESS FOR ITS PREPARATION

[76] Inventors: Kenneth Suk Kang, 6808 Rockglen Ave., San Diego, Calif. 92111; William H. McNeely, 5382 Hewlett Drive, San Diego, Calif. 92115

[22] Filed: Jan. 30, 1975

[21] Appl. No.: 545,454

Related U.S. Application Data

[60] Division of Ser. No. 403,748, Oct. 5, 1973, Pat. No. 3,915,800, which is a continuation-in-part of Ser. No. 239,819, March 30, 1972, abandoned, which is a continuation of Ser. No. 854,322, Aug. 29, 1969, abandoned.

[52] U.S. Cl. .................................. 260/209 R; 8/62; 106/5; 106/148; 106/193 J; 106/193 P; 106/209; 106/214; 195/31 P; 195/96; 252/8.5 C; 252/8.5 M; 252/8.55 D; 252/352; 260/211 R; 426/579; 426/589; 426/599
[51] Int. Cl.$^2$.................. C08B 37/00; C12D 13/04
[58] Field of Search ................................. 260/209 R

[56] References Cited
UNITED STATES PATENTS
3,382,229  5/1968  Patton et al..................... 260/209 R

OTHER PUBLICATIONS
Lopez et al., "Chem. Abst.", vol. 71, 1969, p. 57, 951(f).

*Primary Examiner*—Johnnie R. Brown
*Attorney, Agent, or Firm*—Donald J. Perrella; J. Jerome Behan; Hesna J. Pfeiffer

[57] ABSTRACT

A process for producing a novel heteropolysaccharide by a bacterial fermentation in which a new bacteria is incubated in a final fermentation medium containing a suitable carbohydrate source, a source of magnesium ions, a source of phosphorus and nitrogen, and water, the incubation taking place at a temperature of about 25 to 35°C. for about 35 to 60 hours. The heteropolysaccharide produced by the above process are used to thicken aqueous media. Compositions containing the above polysaccharide in combination with certain salts containing di- and trivalent metal ions are useful for example, in drilling fluids, paint compositions, polishes and as additives for foods.

1 Claim, No Drawings

POLYSACCHARIDE AND BACTERIAL FERMENTATION PROCESS FOR ITS PREPARATION

This is a division of application Ser. No. 403,748, filed Oct. 5, 1973, now U.S. Pat. No. 3,915,800 which in turn is a continuation-in-part of our application Ser. No. 239,819, filed Mar. 30, 1972, now abandoned, which in turn is a continuation application of Ser. No. 854,322, filed Aug. 29, 1969, now abandoned.

The present invention pertains to a novel polysaccharide which is produced by the fermentation of a nutrient medium with a particular species of bacteria. Further, the invention pertains to a novel process of producing the novel heteropolysaccharide by bacterial fermentation under controlled conditions of an aqueous nutrient medium containing carbohydrate. It relates also to compositions containing the new heteropolysaccharide.

It has been known that certain heteropolysaccharides can be obtained by microbial biosynthesis utilizing strains of bacteria. Some of these polysaccharides are of interest as hydrophilic colloids and have been used to thicken, suspend and stabilize water based systems because of their viscosity and rheology properties. See, for instance, U.S. Pat. Nos. 3,659,026; 3,573,972; 3,516,983 and 3,481,889. Research has continued with the objective of discovering new heteropolysaccharides that would likewise be of value as thickeners, suspending agents and stabilizers. It is an object of the present invention to provide such a novel heteropolysaccharide, sometimes referred to herein as Heteropolysaccharide-7. Another object is provision of a method for making Heteropolysaccharide-7 by bacterial fermentation. A still further object is the provision of aqueous systems in which Heteropolysaccharide-7 is present in small amount as a thickening, suspending and/or stabilizing agent. Still other objects of the invention will become apparent from the ensuing description.

It has now been found that a new heteropolysaccharide which we designate as Heteropolysaccharide-7, and which contains glucose, rhamnose and galacturonic acid in an approximate ratio of 6.6:1.5:1, is obtained by fermentation of an appropriate nutrient medium with bacteria designated by us as *Azotobacter indicus* var. *myxogenes*. The bacteria employed in our process is a novel bacteria that was isolated from a sub-surface soil which was fairly rich in organic matter, several days after it has been moistened by rain. A one-gram portion of the soil was added to 13 milliliters of an aqueous solution of a phosphate buffer having a pH of 6.8. The buffered phosphate solution contained 0.5% by weight of $K_2HPO_4$. After adding the soil sample to the buffered solution, it was shaken for a few minutes after which the large soil particles were allowed to settle down. Approximately three milliliters of the supernatant liquid were drawn off and added to a test tube containing 10 milliliters of Nutrient Broth (0.3% by weight of beef extract and 0.5% by weight of peptone in distilled water). The nutrient broth tube was incubated for two hours at room temperature. The broth culture was then streaked on a Yeast-Malt extract agar plate and incubated at 30°C. After about 40 hours of incubation on the agar plate, the gummy colonies which developed on the plate were subcultured. A pure culture was obtained by repeated transfer of bacterial colony to a fresh agar plate of the same medium followed by incubation.

An air-dried film of a 24-hour old culture grown in $E_1$ medium was stained by the method of Gram (Manual of Microbiological Methods, Society of American Bacteriologists, McGraw Hill, New York, N.Y., 1957, page 16). The $E_1$ medium contained 5 grams of potassium acid phosphate, 0.1 gram of magnesium sulfate, 0.9 grams of ammonium nitrate, 0.5 grams Promosoy 100 (an enzymatic digest of soybean meal sold by Central Soya Chemurgy Division), 30 grams of glucose, and 1 liter of tap water. The pH of the medium was 7.6 – 7.8. The Gram staining of the bacteria showed it to be gram negative. When the bacteria were stained by the method of Ziehl-Neelsen, described at page 910 of "Laboratory Methods in Microbiology" by W. Fl Harrigan and M. E. McCance, Academic Press, New York, N. Y. (1966), the bacteria were found to be non-acid fast.

The cells of the bacteria are gram negative, non-sporeforming rods of $0.3 - 0.6 \times 0.5 - 1.2$ microns in size. The bacteria is encapsulated and also produces a large amount of extracellular slime in the $E_1$ medium described previously. The organism is motile, having lateral multitrichous flagella.

The lateral multitrichous flagella were observed by electron microscopic observation at a magnification of 161,000 times. In observing the bacteria under the electron microscope, it was observed by three different methods, i.e., phosphotungstic acid negative staining, uranyl acetate negative staining and platinum-carbon shadowing. These methods are described in "Techniques for Electron Microscopy," Second Edition, edited by D. H. Kay, Blackwell Scientific Publications, Oxford, England (1965). Lateral multitrichous flagellation is illustrated at page 80 of "Modern Microbiology" by W. W. Umbriet, W. H. Freeman & Co., San Francisco, California (1962).

In a nitrate broth (the $E_1$ medium), the organism shows an extensive chain formation up to around 15 bacilli per chain during the logarithmic growth period of the bacteria. In the later stage of the incubation time (the stationary growth period), the organism occurs mostly in ovoid to inflated rod shapes of $0.6 - 0.8 \times 1.2 - 1.6$ microns in size with highly refractive bodies in the cells — usually one at each end. The highly refractive bodies as well as the cell wall components have a normal affinity to safranine dye, which is one of the four staining procedures that is used for Gram staining. consequently, the bacterial cells exhibit a polar staining property on a Gram stained slide. This characteristic is also observed when the bacteria is grown in Burk's medium (Journal of Bacteriology, Volume 27, pages 325–340, 1934) as opposed to growth of the bacteria in the $E_1$ medium.

The colonial morphology of the bacteria was observed by growing the bacteria in two different media. When the bacteria were grown on a YM plate (yeast-malt extract plate), the colonies were observed as shiny, circular yellow colonies having a size of 2–4 millimeters in diameter. The size of the colonies, when grown in this manner, remained relatively constant with time after growing to a size of 2–4 millimeters in diameter. The colonies had a convex elevation with entire margin and, upon aging, the gummy colonies took on a sticky, waxy texture. The yellow pigment found in the colonies is not water soluble but is soluble in ethyl, methyl or isopropyl alcohol. The yellow pigment exhibits a characteristic absorption maxima of 477:446:442 millimicrons when observed by using the absorption procedure of Starr, Journal of Bacteriology, Volume 87, pages 293–302, 1964.

The organism grows well on a plate of Burk's medium in which glucose is substituted on a weight-by-weight basis for mannitol (the standard Burk's medium using mannitol is described in Journal of Bacteriology, Volume 27, pages 324–340, 1934). In growing on a plate of Burk's medium with glucose, the organism develops into gummy colonies which are free of the yellow pigment observed when the colonies were grown on the YM plate. The colonies, as observed on Burk's plate with glucose, are almost transparent and are circular with a size of 2–3 millimeters in diameter, having a pulvinate elevation with entire margin. A poor growth of the bacteria was encountered on a plate of the standard Burk's medium using mannitol. This was evidenced by the growth of lessgummy colonies, with the colonies being less pulvinate and somewhat smaller in size.

The growth characteristics of the bacteria were observed in a number of media. In Nutrient Broth, as described previously, the growth of the bacteria produced a flocculent, slightly turbid media with a small amount of sediment. No odor was observed and there was no surface growth. In a YM broth, the bacteria produced a flocculent, moderately turbid medium with scanty viscid sediment and there was no surface growth. The YM broth was formed by adding 31 grams of a mixture containing 3 parts by weight of a yeast extract, 3 parts by weight of a malt extract, 5 parts by weight of peptone, and 10 parts by weight of dextrose (mixture supplied by Difco Laboratories, Inc., Detroit, Michigan) to 1000 ml. of distilled water. The water was boiled to dissolve the mixture and was then sterilized in an autoclave for 15 minutes at 15 psi, i.e., about 121°C. YM agar, or a YM (Yeast Malt) extract, as referred to previously, is formed in the same manner as the YM broth with the exception that the mixture also contains 20 parts by weight of agar, and 41 grams of this mixture are added to 1000 ml. of distilled water.

When the bacteria were grown in a Nutrient Agar slant composed of Nutrient Broth in admixture with about 1.5% by weight of agar, the bacteria exhibit a filiform growth. When the bacteria were grown on potato ("Manual of Microbiological Methods," by Society of American Bacteriologists, McGraw-Hill, New York, N.Y., 1957, pg. 57) there was a good growth with yellow pigmentation of the bacteria and no darkening of the potato.

The bacteria were also grown on litmus milk (pg. 40 of Harrington & McCance text, supra) resulting in a reduction of the litmus and no clotting and no gas. The growth of the bacteria on potato and in Nutrient Broth, YM broth, Nutrient Agar, YM agar slant and litmus milk as outlined above was carried out at a temperature of 30°C. under aerobic conditions.

In further tests to determine the growth characteristics of the bacteria, the bacteria were cultured in 500 milliliter Erlenmeyer flasks, each containing 100 milliliters of a sterile fermentation medium comprising 100 milliliters of tap water, 0.5 grams of $K_2HPO_4$, 0.01 grams of $MgSO_4$, 0.09 grams of $NH_4NO_3$, and 2.0 grams of glucose. Each of the sterile fermentation media contained an additional source of nitrogen which was varied to determine the ability of the organism to utilize various types of nitrogen. Good growth of the organism was obtained by using an organic nitrogen source such as 0.05 grams of Soy Protein, 0.05 grams of Promosoy, 0.05 grams of peptone, or 0.05 grams of tryptone as the additional source of nitrogen. The soy protein was supplied by Nutritional Biochemical Corp., Cleveland, Ohio, and the peptone and tryptone were supplied by Difco Laboratories, Detroit, Mich. Promosoy is a fat-free soybean powder supplied by Central Soya Co., Chicago, Ill. When an inorganic nitrogen source was employed as the additional nitrogen source, either with or without the additional 0.09 grams of ammonium nitrate, poor growth was obtained. In these tests, 0.05 grams of ammonium sulfate, or 0.05 grams of ammonium nitrate were employed as the sole nitrogen source, either alone or in addition to 0.09 grams of ammonium nitrate.

In the above tests, a loopful of inoculant bacteria was transferred from a YM agar slant culture which had been incubated for approximately 2 to 3 days at a temperature of 30°C. The test conditions under which the organism was grown involved incubation at 30°C. for approximately 35 hours on a rotary shaker having a rotational rate of about 70 R.P.M.

In further tests, the optimum growth temperature of the bacteria was determined on a YM plate and in Burk's medium with glucose, and in $E_1$ broth. It was found that the bacteria will grow under aerobic conditions at temperatures between about 20° to 38°C. No growth was observed at temperatures of 40°C. and the thermal death point of the bacteria was found to be about 55°C. The optimum growth temperature for the bacteria was about 30°C.

The optimum pH conditions for growth of the bacteria were determined in Nutrient Broth. It was found the bacteria grow within the initial pH range of 4.5 to 8.7 while the optimum pH for growth of the bacteria was $7.0 \pm 0.5$. The initial pH of the growth medium in these tests was adjusted by adding HCl or KOH. No further adjustments of the pH were made during the incubation.

In further tests, it was found that the addition of Congo Red dye to a YM plate, followed by streaking the organism on the plate, resulted in colonies which were stained by the dye after an incubation of 30–35 hours under aerobic conditions at about 30°C. The colonies of bacteria were stained a deep orange from the Congo Red dye while the more heavily grown areas on the plate took up less of the dye pigment and had a yellow-orange coloration.

In an additional test, the salt tolerance of the bacteria was determined by inoculating 100 milliliter portions of YM broth medium which contained varying quantities of sodium chloride. The tests were carried out in Erlenmeyer shake flasks having a volume of 500 milliliters. The flasks were each inoculated with 2 drops of a 24-hour cultured organism which had been grown in YM broth using a rotary shaker and a fermentation temperature of about 30°C. These tests showed no growth of the bacteria after 3 days incubation at a concentration of 1% NaCl, and no growth after 6 days at a concentration of 1.5% NaCl.

Antibiotic sensitivity tests were run on the bacteria using a paper disc method. In this procedure, paper discs having a diameter of 5 or 6 millimeters were cut from filter paper and autoclaved to kill any organisms thereon. The autoclaved filter paper was then soaked in a dilute aqueous solution of the antibiotic under test and the impregnated paper disc was placed on the center of a lawn of bacteria in a petri dish and incubated under aerobic conditions for 30 hours at 30°C.

The lawn of bacteria was prepared by first heating YM agar growth medium, as defined previously, to about 100°C. on a water bath to melt it. The liquified agar is then cooled to 45°C. and inoculated by adding a suitable portion of a YM broth culture of the bacteria which was then thoroughly mixed and poured into a sterile petri dish. The agar is then solidified by cooling to room temperature and, after solidification, there is obtained, on incubation, a hazy, homogeneous-appearing bacterial growth. The term "lawn" refers to such a preparation which contains a very high bacterial count.

After incubation of the solidified agar at 30°C. for about 24 hours in the petri dish in contact with the impregnated disc, as described above, the bacterial growth was observed. If the bacteria were sensitive to the antibiotic, there was a clear area around the periphery of the disc which was free from bacteria. Determination of antibiotic sensitivity by the above method is described in the literature at pages 154-155 of the Harrigan and McCance text, supra.

When tested in the above manner, it was found that the bacteria employed in the present invention were not sensitive to penicillin, polymyxin B, neomycin sulfate, or cyclohexamide. However, the bacteria were found to be sensitive to streptomycin and aureomycin.

In further tests, the biochemical characteristics of the bacteria were determined. The bacteria tested positive to the Methyl Red test procedure described at page 60 of the Harrigan and McCance text, supra. The bacteria gave a positive catalase text, a negative urease test, a positive oxidase test, a negative amylase test, and a positive cellulase test. The catalase, urease, oxidase and amylase tests are set forth, respectively, at pages 65, 56, 65 and 58 of the Harrigan and McCance text. The bacteria also gave a positive arginine hydrolase test after 5 days at aerobic conditions according to the method of M. J. Thornley, "Journal of Applied Bacteriology," Volume 23, page 37 (1960). The bacteria gave a negative indol formation test, a negative gelatin liquefaction test, a negative nitrate reduction test, a positive $H_2S$ formation test, a negative citrate utilization test, and a negative acetylmethyl carbinol formation test. The indol formation, gelatin liquefaction, nitrate reduction, $H_2S$ formation, citrate utilization and acetylmethyl carbinol formation tests are set forth, respectively, at pages 53, 51 and 52, 56 and 57, 55 and 203 and 60 of the Harrigan and McCance text, supra.

The cellulase test which was employed is not a standard test. In performing the test, a citrate buffer solution having a pH of about 6.5 was made up which contained 1.75% by weight of hydroxyethyl cellulose. To this was added a 1.75% by weight aqueous solution of heteropolysaccharide gum as produced by the bacteria employed in the practice of the present invention. The gum solution and the hydroxyethyl cellulose solutions were mixed in the ratio of 3 parts by weight of the hydroxyethyl cellulose solution to 1 part by weight of the gum solution. The mixed solutions were then incubated at 43.3°C. in a tightly sealed jar for at least 4 days. The presence of the cellulase enzyme will result in degradation of the hydroxyethyl cellulose, thereby reducing the viscosity of the mixed solutions. By noting that there was, in fact, a decrease in the viscosity of the mixed solutions in excess of about 5%, it was determined that the cellulase enzyme was present and was produced by the bacteria employed in the present invention. In performing the test, a preservative containing 1-(3-chloroallyl)-3,5,7-triaza-1-azoniaadamantane chloride (Dowicil 100 supplied by the Dow Chemical Co.) was added at 0.2% by weight to kill any bacteria in the solutions so that the only agent present which could cause degradation of the cellulose was the cellulase enzyme.

Jars which contained only the substrate hydroxyethyl cellulose solution were subjected to the same conditions as the mixed solutions to furnish test controls.

In a further series of experiments, the bacteria were grown in various basal media containing a carbohydrate source. The growth of the bacteria was observed to determine whether the bacteria sustained poor growth, fair growth or good growth, and the pH of the media were measured to determine whether growth of the bacteria produced an acid condition, an alkali condition, a weak acid condition, or essentially no change in the pH.

In conducting the above experiments concerning the utilization of various carbohydrate sources by the bacteria, the basal medium described by D. W. Dye, New Zealand J. of Science, Vol. 5, gates 393–416 (1962), was first sterilized by autoclaving. A carbohydrate solution was then made up and was sterilized by filtration through a Seitz filter pad in which the holes passing through the filter pad are approximately 1/50th micron in diameter. No living bacteria is sufficiently small to permit its passage through a Seitz filter pad. Thus, filtration in this manner is a convenient way to sterilize an aqueous medium without the use of heat.

The sterilized carbohydrate solution was then added to the basal medium described by Dye in a sufficient amount to give a total carbohydrate concentration of 0.5% by weight. The pH of the growth medium was adjusted to about 7 and there was then added a few drops of Brom-Cresol Purple, which was used at the pH indicator. Following this, the growth medium as contained in an agar slant was streaked with bacteria, the test tube was closed, and the organism was incubated at 30°C. The results of these tests are shown in the following Table I.

TABLE I

| Carbohydrate | Time (days) | | | | |
|---|---|---|---|---|---|
| | 1 | 2 | 3 | 4 | 5 |
| D-glucose | A (+++) | | | | |
| D-mannose | A (+++) | | | | |
| D-galactose | A (+++) | | | | |
| D-fructose | A (+++) | | | | |
| D-arabinose | A (+++) | | | | |
| D-xylose | A (+++) | | | | |
| D-ribose | | | | | WA (++) |
| L-rhamnose | | | | | WA (++) |
| D-sucrose | A (+++) | | | | |
| D-maltose | A (+++) | | | | |
| D-trehalose | A (++) | | | | |
| D-lactose | | | A (+++) | | |
| D-cellobiose | A (+++) | | | | |
| D-melibiose | | | | A (++) | |
| D-raffinose | | | A (+++) | | |
| Dextrin | | | | | WA (++) |
| Salicin | | | A (+++) | | |
| Na-Alginate | | – (++) | | | – (++) |
| D-mannitol | Alk (+) | | | | |
| i-inositol | Alk (+) | | | | |
| adonitol | Alk (+) | | | | |

A = Acid;
Alk = Alkali;
WA = weak acid;
– = no change
(+) poor growth
(++) fair growth
(+++) good growth As shown in the above table, the bacterium is able to utilize a wide variety of carbohydrates for growth. Certain types of carbohydrates are, however, utilized more effectively than others, and the resulting pH of the medium varies depending upon the carbohydrate source employed. The pH indicator, Brom-Cresol Purple, gives a yellow coloration at an acid pH of less than 5.2, and a violet coloration at a pH higher than 6.8 denoted above as alkali. Within the pH range of 5.2 to 6.8, the indicator has a bluish-green coloration. The designation weak acid (WA) employed in the above table, indicates a coloration of the medium, which is a composite of bluish-green and yellow, indicating that the acidity of the medium is not sufficiently low to produce the characteristic yellow coloration that occurs with a pH of less than 5.2. In the above tests, control tests were carried out under the same conditions with the same media without the presence of the bacteria. The control tests showed no change in the pH during incubation; thus, indicating that the resultant pH change was caused by the bacteria.

In still further tests, the bacteria employed in the present invention was grown on the Burk's agar containing glucose on an equal weight basis in lieu on mannitol, as described previously. The tests were carried out on Burk's agar plate to which was added a specified weight of an amino acid which was blended with the agar and allowed to solidify. The sterile agar plates were streaked with the bacteria and incubated at 30°C. under aerobic conditions for 72 hours. The results of these tests are shown in the following Table II.

TABLE II

| Amino acids | Growth | | Pigmentation |
|---|---|---|---|
| Glycine | − | | |
| DL-Alanine | − | | |
| DL-Serine | − | | |
| DL-Threonine | + | (very poor) | no pigmentation |
| DL-Valine | − | | |
| DL-Leucine (1,0.5) | + | | pale yellow |
| L-Isoleucine (1,0.5) | + | | pale yellow |
| DL-phenylalanine | + | (very poor) | no pigmentation |
| DL-Tyrosine (1,0.25) | + | | yellow |
| L-Cystine (1,0.17) | + | | pale yellow |
| DL-methionine | − | | |
| DL-Tryptophan | + | | no pigmentation |
| L-Proline | + | | pale yellow |
| L-Hydroxyproline | + | | pale yellow |
| DL-Aspartic acid | + | | bright yellow |
| L-GLutamic acid | + | | bright yellow |
| DL-Histidine | − | | |
| L-Lysine | − | | |
| L-Arginine | + | | bright yellow |
| L-Citruline | + | | yellow |

+ : Growth
− : No growth

As shown in the above Table II, the effect of individual amino acids on the growth of the bacteria varies considerably. Some amino acids, such as glycine, and serine, have an adverse effect upon the bacteria and prevent their growth. Other amino acids, such as tryptophan and threonine seemed to have little effect on the bacteria since their growth in Burk's medium produced colonies having no pigmentation. Still other amino acids had a striking effect upon the growth of the bacteria, as evidenced by the color of the colonies produced. Some amino acids, such as leucine, isoleucine, cystine, and hydroxproline, were utilized to some degree in the growth of the bacteria to produce a pale yellow pigmentation of the colonies. Tyrosine and citruline were utilized by the bacteria to produce a pigmentation of the colonies which was more pronounced and had a yellow pigmentation. Still other of the amino acids, such as aspartic acid, glutamic acid and arginine, have an even more pronounced effect to produce a bright yellow pigmentation in the resulting colonies. The specificity of the bacteria in utilizing particular amino acids is quite remarkable. Thus, for example, the bacteria utilize arginine to produce a bright yellow pigmentation of the colonies but does not utilize the closely related amino acid lysine. Surprisingly, lysine is not utilized by the bacteria, but is found to have a harmful effect since it inhibited bacterial growth.

As indicated in the above table, certain of the tests were repeated while using the amino acid at a reduced concentration less than 1% by weight. The results of the tests at the reduced concentrations indicated were essentially the same as the results at the 1% concentration.

The above information regarding the bacteria employed in the present invention is summarized in the following Table III.

TABLE III

Characteristics of the Bacteria

Morphology
a. Cells—Gram negative, non-acid fast, nonspore forming rod of 0.3–0.6 × 0.5–1.2 $\mu$ in size. Bacteria is encapsulated and produces a large amount of extracellular slime. Organism is motile having lateral multitrichous flagella. In a nitrate broth organism shows an extensive chain formation up to around 15 bacilli per chain only during the logarithmic growth period. In the stationary growth period of the incubation time organism occurs mostly in an ovoid to inflated rod shapes of 0.6–0.8 × 1.2–1.6 $\mu$ in size with highly refractive bodies in the cells—usually one at each end. These bodies and cell wall component have a normal affinity to Safranine dye while the rest have very weak or no affinity at all. Consequently, organism exhibits a polar staining property on a gram stained slide. This characteristic also observed in the bacteria grown in Burk's medium.
b. Colony—The following colonial morphology is observed on the two different media.
YM plate: Shiny circular yellow colonies with a size of 2–4 mm. in diameter. Convex elevation with entire margin. Gummy colonies develop a sticky waxy texture upon aging. Yellow pigment is not water soluble but soluble in alcohols. It exhibits a characteristic absorption spectrum (477:446:442 m$\mu$).
Burk's plate with glucose: Organism grows well developing into gummy colonies free of the yellow pigment. Colonies are almost transparent and circular with a size of 2–3 mm. in diameter; pulvinate elevation with entire margin. Poor growth encountered on the Burk's medium with mannitol as carbon source.

Growth Characteristics
a. Nutrient broth—flocculent, slightly turbid with small amount of sediment. No odor or surface growth.
b. YM broth—flocculent, moderately turbid with scanty viscid sediment. No surface growth.
c. Nutrient agar slant—filiform growth.
d. YM agar slant—filiform growth.
e. Potato—good growth with yellow pigmentation and no darkening of potato.
f. Litmus milk—reduction of litmus, no clotting, no gas. Casein hydrolysis with clear upper layer.
g. Nitrogen source—good growth in shake flask with organic nitrogen source such as peptone, tryptone, and soy proteins. Poor growth with inorganic nitrogen such as ammonium sulfate or ammonium nitrate. The pigmentation is associated with nitrogen, particulary the inorganic source.
h. Growth temperature—grow at 20–38°C. No growth at 40°C. The optimum temperature is around 30°C. Thermal death point is around 55°C.
i. Growth pH—grow in nutrient broth in the pH range of 4.5 to 8.7. The optimum pH is 7.0 ± 0.5.
j. Congo red absorption—colonies stained deep orange, more heavily grown area takes up less pigment, yellow-orange.

Salt Tolerance
   YM broth containing:
1.0% NaCl—no growth after 3 days incubation.
1.5% NaCl—no growth after 6 days incubation.
Antibiotic Sensitivity
   Penicillin                    not sensitive TABLE III-continued

| | |
|---|---|
| Polymyxin B | not sensitive |
| Streptomycin | sensitive |
| Aureomycin | sensitive |
| Neomycin sulfate | not sensitive |
| Cyclohexamide | not sensitive |
| Biochemical Characteristics | |
| Methyl red | positive |
| Catalase | positive |
| Indol formation | negative |
| Urease | negative |
| Arginase | positive (5 days, aerobic) |
| Oxidase | positive |
| Amylase | negative |
| Cellulase | positive |
| Gelatin liquefactation | negative |
| Nitrate reduction | negative |
| $H_2S$ formation | positive |
| Citrate utilization | negative |
| Acetylmethyl carbinol formation | negative |

Carbonhydrate Utilization in Dye's Medium at 0.5%
Concentration of carbohydrate using Brom-Cresol Purple
Good growth in one day to produce acid
pH: D-glucose, D-mannose, D-galactose,
D-fructose; D-arabinose, D-xylose, D-sucrose,
D-maltose, and D-cellobiose
Fair growth in one day to produce acid pH
using D-trehalose
Poor growth in one day to produce alkaline pH:
D-mannitol, i-inositol, and adonitol
Good growth in three days to produce acid pH:D-lactose,
D-raffinose, and salacin
Fair growth in four days to produce acid pH using
melibiose
Fair growth in five days to produce weak acid pH:
D-ribose, L-rhamnose, and dextrin
Fair growth in either two or five days to produce
essentially no change in pH using sodium alginate.

Effects of Amino Acids on Pigmentation and growth of
Bacteria in Burk's agar with glucose
No growth with glycine, alanine, serine, valine,
histidine, lysine, methionine
Very poor growth with phenylalanine and no
pigmentation
Growth with leucine, isoleucine, cystine, and
hydroxyproline to give pale yellow pigmentation;
with tyrosine and citruline to give yellow
pigmentation; with aspartic acid, glutamic acid
and arginine to give bright yellow pigmentation.

On the basis of the above tests, it has been attempted to identify the bacteria in terms of morphological characteristics and physiological properties, as compared with those of known organisms recorded in the Bergey's Manual of Determinative Bacteriology, reprint of 7th Ed., Williams & Wilkins Co., Baltimore, Md. (1959). Since the new bacteria is a rod-shaped rigid cell, non-acid-fast, and motile by means of non-polar flagella, the bacteria is properly placed in the Order of Eubacteriales. For this reason, the Order Pseudomonadales is excluded. Among the Order Eubacteriales, there are four Families which have been given close examination. These Familes are Achromobacteracae, Enterobacteriaceae, Rhizobiaceae, and Azobacteriaceae. The organisms belonging to these families are discussed individually in comparison to the novel bacteria employed in the present invention.

I. Family Achromobacteraceae

The chromogenic organisms which do not attack agar or aliginates are characterized as the Genus Flavobacterium. Some species of this Genus have a few similarities to the novel bacteria employed in the present invention with respect to the water insoluble, alcohol-soluble carotenoid pigment produced by the bacteria and the fact that they do not produce gas from a carbohydrate medium according to the usual culture tests. However, they have the following dissimilarities. Flavobacteria do not grow on Burk's plate and they do not undergo the morphological transformations, i.e., they do not alter their shape or size during growth. There are three species of the Genus which are motile, gelatin not liquified and non-marine forms. It should be remembered at this point that the bacteria employed in the present invention does not grow in a medium containing 2% by weight of sodium chloride which excludes the marine forms. The three species of flavobacteria are *F. harrisonii*, *F. invisible*, and *F. lactis*. *F. harisonii* turns glucose, lactose, maltose and sucrose broth alkaline whereas the present bacteria turns these media acid. They have an optimum growth temperature of 25°C. as compared with 30°C. for the present bacteria. *F. invisible* produces white colonies on an agar plate and does not change litmus milk. Also, it does not grow on potato. *F. lactis* shows a thick growth with slimy brownish color with yellowish margin on potato and the organism has a characteristic pleasant odor, while the bacteria employed in the present invention has an unpleasant odor.

II. Family Enterobacteriaceae E.

Erwinia is the only Genus in the Family Enterobacteriaceae which produces a characteristic yellow pigment. All of the yellow pigmented Erwinia species, such as *vitivora*, *milletiae*, *cassavae*, *ananas*, *citrimaculans*, and *magniferae*, are capable of reducing nitrate to nitrite and producing acid from mannitol. Also, they produce acid from lactose broth, except *cassavae* and *citrimaculans*. However, *E. cassavae* is not encapsulated and is methyl red negative while *e. citrimaculans* is indole positive.

III. Family Rhizobiaceae

The Genus Rhizobium is ruled out due to the following reasons. All of the recorded Rhizobia, except *R. lupini* grow rapidly on mannitol agar plates. Rhizobia do not produce hydrogen sulfide and they lose the capability of fixing atmospheric nitrogen on their transfer to a laboratory medium. Rhizobia grow well on YM medium containing 2% by weight of sodium chloride. Rhizobium species with the exception of *R. melitoti* grow poorly and show no growth after 24 hours on glucose-peptone agar, which is similar to Nutrient Agar used for growth of the present bacteria. Most Rhizobia fail to absorb Congo Red on yeast-extract mannitol agar, as described by Gibbs and Shapton, "Identification Methods for Microbiologists," Academic Press, New York, N.Y., 1968, page 53). No Rhizobium produces carotenoid yellow pigment, similar to that produced by the bacteria used in the present invention.

*Agrobacterium gysophila* is the only species of the Genus Agrobacterium recorded in the Bergey's Manual which produces a yellow pigment (reported as "Naple Yellow"). However, this bacteria produces nitrite from nitrate, can utilize citrate as the sole source of carbon in its growth, and grows well on yeast extract-mannitol agar containing 2% by weight of sodium chloride.

IV. Family Azotobacteraceae

The bacteria employed in the present invention has a morphology and growth characteristic which more closely resembles those of Azotobacter indicus. Both organisms show vacuolated and polarly stained cells. Also, they both grow well on Burk's plate with abundant gum formation. However, the following dissimilarities have been observed.

a. *A. indicus* grows better on Burk's plate with mannitol as the carbon source than with glucose as the carbon source. The bacteria of the present invention show an opposite growth pattern, i.e., they grow better on Burk's plate with glucose as the carbon source than with mannitol.

b. The bacteria of the present invention produce colorless, more or less, transparent colonies on the Burk's plate medium, but produce yellow pigment in a medium containing nitrogen in the form of certain amino acids or an inorganic nitrogen source such as ammonium nitrate. *A. indicus* forms light-brown to greyish-white colonies on Burk's plate and does not produce the yellow pigment on a medium such as a YM plate which contains a wide variety of amino acids.

c. The size of an old A. indicus culture on Burk's plate is larger than that of a culture of the bacteria of the present invention when grown on the same medium.

d. *A. indicus* does not grow in Nutrient Broth as do the bacteria of the present invention.

In general, *A. indicus* grows poorly in a protein-containing media as compared to growth in a nitrogen-free media such as Burk's medium. The growth pattern of the bacteria of the present invention is opposite, in that the bacteria grow well, in general, in a protein-containing media as compared with a nitrogen-free medium.

Some strains of Pseudomonas produce a non-diffusable yellow pigment. However, these Pseudomonas species have been ruled out based on the fact that they are polarly flagellated and are sensitive to the antibiotic Polymyxin B. (Gibbs & Shapton, "Identification Methods for Microbiologists," Academic Press, 1968, page 72).

On the basis of the above testing of the bacteria of the present invention, and a comparison of their morphological characteristics and physiological properties with those of known bacteria, it is our belief that the bacteria employed in the present invention are a new type of bacteria of the Family Azotobacteriaceae. Because of its resemblance in many respects to *Azotobacter indicus*, but having in mind as well the points of difference, our new organism has been named *Azotobacter indicus* var. *myxogenes*. A deposit of a strain of the bacteria of the present invention was made in the American Type Culture Collection on Aug. 19, 1969 and the accession number of the deposit is 21423.

In practicing our invention, Heteropolysaccharide-7 is produced by growing the *Azotobacter indicus* var. *myxogenes* organism in an aqueous nutrient medium at a temperature of from about 25°–35°C., and preferably at about 30°C. until substantial Heteropolysaccharide-7 is elaborated. The fermentation time is normally from about 35–60 hours, and preferably from 37–48 hours.

The aqueous nutrient medium, i.e., the fermentation medium, contains an appropriate source of carbon and nitrogen as well as a source of low levels of magnesium and phosphorus. The carbon source is a carbohydrate at a concentration of about 1 to 5% by weight, and preferably about 2 to 3% by weight. Suitable carbohydrates include, for example, dextrose, sucrose, maltose, fructose, mannose, starch hydrolysate or corn syrup. Preferably, the carbohydrate source employed is dextrose (glucose). Crude sugars may be used, such as deionized molasses, or a product such as Hydrol-E-081 manufactured by Corn Products Refining Company. Hydrol-E-081 is a mixture composed largely of dextrose and maltose and includes small amounts of oligosaccharides. A further ingredient which is present in the fermentation medium is a source of magnesium ions. The magnesium salt content of the fermentation medium is in the range of about 0.005 to about 0.02% by weight. The source of magnesium ions is not critical, and suitable sources include water soluble magnesium salts, such as magnesium sulfate heptahydrate, magnesium acetate, magnesium chloride, magnesium nitrate, and magnesium acid phosphate.

At least a trace quantity of phosphorus, generally in the form of a soluble potassium salt, is also present in the fermentation medium. Larger quantities of phosphorus, such as about 0.65% by weight of the fermentation medium, calculated as dipotassium-acid-phosphate, can, however, also be used without adverse effects.

A further ingredient which is present in the final fermentation medium is a source of nitrogen. The nitrogen source may be organic in nature as, for example, soy protein; an enzymatic digest of soybean meal such as Soy Peptone, Type-T; Promosoy 100; a pancreatic hydrolysate of casein, such as N-Z amine Type A; an enzymatic digest of proteins, such as Ferm Amine Type IV, or distillers solubles, such as Stimuflav. Soy protein is sold by Nutritional Biochemical Corp., Cleveland, Ohio; Promosoy 100 is sold by Central Soya Chemurgy Division; Stimuflav is marketed by Hiram Walker & Sons, Inc., and the other materials are sold by Sheffield Chemmical, Norwich, N.Y. When utilizing an organic nitrogen source in the fermentation medium it may be present in an amount ranging between about 0.01 and about 0.07% by weight of the fermentation medium.

Also, it has been found desirable to have present in the fermentation medium an inorganic nitrogen source, such as ammonium nitrate, ammonium chloride, ammonium sulfate or ammonium acetate. The amount of ammonium salt which may be employed can range from about 0.02 to about 0.15% by weight and preferably from about 0.045 to about 0.1% by weight of the medium.

The pH of the fermentation medium is important for suitable growth of the bacteria and elaboration of Heteropolysaccharide-7. We have found that the optimum starting pH for production of colloid is within the range of about 7 ± 0.5. Control of the pH within this range can generally be obtained by the use of a buffer compound such as dipotassium acid phosphate at a concentration from about 0.4 to about 0.6% by weight of the fermentation medium. Conversely, the pH can be controlled through conventional means by using a pH meter coupled with a source of a suitable base, such as a solution of potassium hydroxide. As the pH is lowered due to the production of acids during the fermentation reaction, small quantities of the potassium hydroxide solution may be automatically added by the pH controller to keep the pH within the desired range.

Typically, the bacterial fermentation process of our invention under the above conditions does not require the addition of alkali to neutralize the acid throughout the entire course of the fermentation. However, the pH of the fermentation liquor does drop gradually down to about 6.0 and this generally occurs during the latter part of the fermentation (for example, if the fermentation is allowed to exceed 40 to 45 hours). However, this is considered as normal. In the event, however, that the pH should drop below 6.0 after about 35 to 40 hours of incubation, this is an indication of an abnormal fermentation and, in this case, potassium hydroxide or another suitable base such as sodium hydroxide should be added so as to maintain a pH of at least about 6.5.

In order to obtain a rapid fermentation, we have found that it is essential to have a sufficient quantity of oxygen available for the growing *Azotobacter indicus* var. *myxogenes* culture. If either too much or too little oxygen is available, the production of Heteropolysaccharide-7 by the bacterial culture is slowed down. Our process requires that sufficient oxygen be made available for the bacteria. The oxygen requirements can be defined in terms of a sulfite oxidation value, which is a measure of the rate of oxygen uptake in the fermentor under the agitation and aeration conditions employed. It is, however, preferred to describe this aspect of the process in terms of dissolved oxygen, and in this regard it is important that a dissolved oxygen level of 5–10% be maintained at least during the first 20–40 hours of the fermentation. Thus, the liquid medium should contain 5–10% of the amount of oxygen that can be dissolved in the medium, when the oxygen is added as air.

The course of the fermentation to produce our novel heteropolysaccharide may be followed by determining the residual sugar content of the fermentation medium. For best results, the fermentation is continued until the residual sugar content of the medium is in the order of about 0.3% by weight, and preferably in the order of about 0.1% by weight or less.

When the fermentation is completed, our novel Heteropolysaccharide-7 may be recovered from the fermentation liquor by known techniques, and preferably by solvent precipitation. Thus, the fermentation beer is treated with a water miscible solvent which does not react with the heteropolysaccharide and in which the product is only slightly soluble. The product is thus precipitated and may be recovered by accepted and known techniques, and dried. Typical organic solvents which may be used for this purpose are straight or branched chain lower alkanols, i.e. methanol, ethanol, isopropanol, butanol, t-butanol, isobutanol, n-amyl alcohol of which isopropanol is the preferred alcohol; lower alkyl ketones, such as acetone, may be employed. In some cases the precipitation is improved if the fermentation medium is first heated to a temperature of about 70°–90°C. for a short period of time and then cooled to about room temperature before addition of the solvent.

The novel Heteropolysaccharide-7 obtained as described above is a high molecular weight polysaccharide that functions as a hydrophilic colloid to thicken, suspend and stabilize water based systems. It is slightly soluble in lower alkanols and acetone. The carbohydrate portion of the molecule consists of about 73% of glucose, about 16% of rhamnose and about 11% of a uronic acid (all by weight). Thus, the glucose, rhamnose, uronic ratio may be expressed as 6.6:1.5:1.0. It has an acetyl content of about 8.0–10.0%.

The acetyl content is determined by treating a 0.1% aqueous solution in an oxygen-free atmosphere with a known volume of 0.01 N potassium hydroxide containing 1% (W/V) potassium chloride at room temperature. Aliquots are removed at elapsed time intervals and the acetyl content determined by back-titration with 0.01N sulfuric acid.

The composition of the carbohydrate portion of Heteropolysaccharide-7 is determined by dissolving 0.5 grams of the product in 100 ml. of water. 100 ml. of 4N sulfuric acid is added to the resulting solution, and the mixture refluxed for 12 hours. The resulting solution is cooled and brought to pH 5-6 with barium carbonate. The resulting precipitate of barium sulfate is separated by filtration and barium ions removed from the filtrate using a cation exchange resin on the hydrogen cycle. After removal of the resin, the solution is concentrated to a syrup under reduced pressure at 35°C., and the sugars are tentatively identified by paper chromatography.

60 mg. of the above hydrolysate syrup is dissolved in 10 ml. of water and the sugar is reduced by treating with 150 mg. of sodium borohydride for 12 hours. After decomposition of excess sodium borohydride by treatment with Amberlite IR-120 on he hydrogen cycle, the residual boric acid is removed by co-distilling several times with methanol. The resulting alditols are acetylated by treating with 5 ml. of acetic anhydride in 5 ml. of pyridine for 12 hours. Water is then added to the reaction mixture which is then concentrated to a small volume and co-distilled several times with chloroform. The resulting residue is dissolved in chloroform and gas liquid chromatography performed with a Hewlett-Packard Model 5750 chromatograph using 3% by weight of ECNSS-M on 80/100 Gas Chrome Q at 185°C. The sugars are identified by comparison with authentic standards and the proportions of alditol acetates determined directly from the peak areas on the gas chromatogram by integration.

That Heteropolysaccharide-7 contains glucose, rhamnose (in an approxiamte 4–5.5:1 molar ratio) was also determined by paper chromatography with the solvent system n-butanol: pyridine:$H_2O$ in the ratio of 2:2:1. These results were confirmed in two other solvent systems and in a gas chromatographic analysis with silyl derivatives of an acid hydrolysate of the heteropolysaccharide.

Heteropolysaccharide-7 is also characterized by its viscosity and pseudoplasticity properties which appear in the detailed examples.

The further illustrate our invention, we have presented the following examples of which all parts and percentages are by weight unless otherwise indicated.

EXAMPLE 1

100 milliliters of a seed culture medium was made up in a 500 milliliter Erlenmeyer flask. The composition of the seed fermentation medium was as follows: $K_2HPO_4$ — 0.5%; $MgSO_4.7H_2O$ — 0.01%; $NH_4NO_3$ — 0.09%; Promosoy — 0.05%; glucose — 2.00%, and water — the balance. In making up the seed culture medium, the glucose in admixture with a portion of the water was sterilized separately by steam sterilization and was then added to the other ingredients contained in the balance of the water, which had also been steam sterilized.

The sterile seed medium was then inoculated aseptically with *Azotobacter indicus* var. *myxogenes* ATCC 21423 by means of a monocolony transfer from a vigorously growing culture on a YM plate. The flask was then incubated under aerobic conditions on a rotary shaker for approximately 35 hours at 30°C.

In the event that the inoculum bacteria is started from a lyophile or a long-refrigerated slant culture, several plate-to-plate transfers may first be made before aseptically inoculating the seed culture medium.

Following incubation on a rotary shaker for approximately 35 hours at 30°C., a fresh seed medium having the same composition and volume as employed in Example I may be inoculated aseptically with 1 milliliter of the fermentation liquor obtained from Example I and the fermentation repeated under the conditions of Example I.

EXAMPLE II

In scaling up the fermentation, a 4-liter capacity Fernback flask containing 1 liter of a seed culture medium, as defined in Example I, is inoculated with 100 milliliters of a small-flask culture prepared as described in Example I. If desired, and generally this is preferable, the small-flask culture used for the inoculant has been grown in two stages. The first stage is as described in Example I and in the second stage 1 milliliter of the beer produced by Example I is used to inoculate a fresh medium which is incubated in the same manner as Example I for 25 to 30 hours. After inoculating the 1-liter of medium in the Fernbach flask, the flask is incubated on a reciprocal shaker at 30°C. for 25–30 hours.

EXAMPLE III

A 10-gallon fermentor having a 6-gallon working capacity, was inoculated with the contents of the beer produced in the manner described in Example II. The composition of the growth medium in the 10-gallon fermentor is the same as that described in Example I and the total volume of the fermentation medium, including the volume of the inoculant produced by Example II, was about 6 gallons. The 10-gallon fermentor was then incubated for 24–30 hours at about 30°C. at an agitation rate of about 900 feet per minute tip speed of the turbine impeller and an aeration rate of 0.7 cubic feet per minute. An antifoam agent (Nopco 1419A, supplied by Nopco Chemical Co.) was employed in the 10 gallon fermentor at a total concentration of 10 milliliters. The antifoam agent is a blend of hydrocarbon and nonionic ester emulsifier.

EXAMPLE IV

About 6 gallons of a 30-hour old culture prepared as in Example III was used as the inoculant for a 100 gallon working capacity fermentor. The fermentor contained about 100 gallons of a fermentation medium having the same composition as defined in Example I, including the inoculant from Example III. The total concentration of antifoam agent (Nopco 1419A) was 600 milliliters. The aeration rate during the first 10 hours of the fermentation at about 30°C was 7½ cubic feet per minute. The fermentation was then continued for an additional 15 to 20 hours at an aeration rate of 10 cubic feet per minute. During the entire fermentation, the agitation rate was about 865 ft. per minute at the tip of the turbine impeller.

EXAMPLE V

The fermentation beer produced in Example IV was charged to a 1500 gallon fermentor having a working capacity of 1200 gallons and containing about 1100 gallons of a medium the same as that described in Example I with the exception that the glucose concentration is 3% by weight on an anhydrous basis of the total weight of the fermentation medium. The total quantity of fermentation medium is sufficient to make up the volume of about 1200 gallons, including the volume of the seed culture. The fermentation temperature was maintained at about 30°C. and during the first 10 hours of the fermentation, the aeration rate was 40 cubic feet per minute and the speed of agitation was about 1400 ft. per minute at the tip of the turbine impeller. After 10 hours, the aeration rate was increased to 80 cubic feet per minute and the agitation rate remained the same. The progress of the fermentation was followed by determining the residual sugar content of the fermentation medium. Fermentation was completed at the end of about 48 hours when the residual sugar content had dropped to about 0.1% (determined by Lane & Eynan copper reduction method—Chemistry & Industry, pgs. 32–35, 1923), and the viscosity of the fermentation beer had increased to in excess of about 4500 cps.

At the end of this time, the Heteropolysaccharide-7 was recovered by adding isopropyl alcohol to the fermentation beer to provide about 57 to 65% by weight of alcohol in the spent beer. This resulted in precipitation of the heteropolysaccharide. The precipitated fibrous Heteropolysaccharide-7 was then separated from the spent fermentation beer and was pressed to express the excess alcohol.

EXAMPLE VI

A 24-hour seed medium was prepared by growing *Azotobacter indicus var. myxogenes* ATCC 21423 in an aqueous nutrient medium having the composition:

| | |
|---|---|
| potassium acid phosphate | 5 grams |
| magnesium sulfate haptahydrate | 0.1 gram |
| ammonium nitrate | 0.9 gram |
| Promosoy 100 (enzymatic digest of soybean meal) | 0.5 gram |
| dextrose | 30 grams |
| tap water | to 1 liter | following the procedures of Examples I and II. After a 24-hour growth period. 200 ml. of this seed medium was used to inoculate a 5 liter fermentor containing 2800 ml. of the above medium. The inoculated fermentation broth was aerated at the rate of 2 liters per minute, and the fermentation temperature maintained at 30°C. The mixture was agitated at a rate of 260 feet per minute (tip speed), this being increased to a maximum of 780 feet per minute as necessary to insure adequate mixing during the fermentation. Fermentation was continued for a period of 56 hours at which time the viscosity of the broth was 7000 cps with a pH of 6.4. At this time the fermentation liquor was added to about 9 liters of isopropanol, with vigorous agitation, in order to precipitate the heteropolysaccharide. On completion of the precipitation, the desired Heteropolysaccharide-7 was recovered by pressing, and dried at an elevated temperature. It has a reconstituted viscosity in water of 1100 cps. (0.75% solution).

The viscosity of our heteropolysaccharide may be lowered, if desired, by following the procedure of Example V, and aging the fermentation beer for about 24 hours at about 20°–30°C. after completion of the fermentation (as determined by low residual sugar content) prior to precipitation of the product. The lower viscosity is preferred in some instances when the heteropolysaccharide is used as an additive to water-base paint. Alternatively, the viscosity of the final product may be reduced by conducting the fermentation at a slightly higher temperature, e.g. about 33°–34°C.

If desired, the fermentation beer resulting from the procedures of Example V and VI, or from the alternative procedures described above, i.e., holding for about 24 hours after completion of the fermentation, or increasing the fermentation temperature to 33°–34°C., may be heated by passage through a heat exchanger maintained at about 75°–82°C. with a holding time of approximately 15 to 20 minutes. This step may be advantageously employed prior to the precipitation of Heteropolysaccharide-7 by the addition of a lower alkanol since holding at the higher temperature has been found to inactivate cellulase enzyme produced by the bacteria.

An effective amount of a preservative, such as formaldehyde, may, and preferably is, added to the fermentation medium on completion of the fermentation. Suitable amounts are, for example, about 2 to about 5 milliliters of formaldehyde per liter of fermentation medium. This addition may take place before holding the medium for about 24 hours as described above, or before separating the heteropolysaccharide from the medium.

Following recovery of the polysaccharide by any suitable method such as filtration, centrifugation, or sieving, and pressing of the polysaccharide to remove excess alcohol, the polysaccharide may be dried by any suitable manner such as, for example, in a tray dryer at a temperature of about 60°C. followed by milling. It is obtained as a pale cream colored powder readily soluble in cold or hot water.

The novel Heteropolysaccharide-7 produced by the method of our invention, as described above, has a number of unusual properties. It is soluble in aqueous media at varying concentrations to produce viscous media which are highly pseudoplastic, i.e., the viscosity of the aqueous media changes immediately with respect to shear rate. Also, the viscosity of an aqueous medium containing the heteropolysaccharide has been found to be remarkably stable over the temperature range from 4° to 90°C. Freezing and thawing of the aqueous media has only a slight affect on the viscosity and, in general, the heteropolysaccharide shows very good thermostability.

To demonstrate the relationship between the concentration of the heteropolysaccharide and the viscosity which it produces in an aqueous system, we present the following data in Table IV. As shown in this table, aqueous solutions were prepared containing varying concentrations of Heteropolysaccharide-7 and the viscosities of the aqueous solutions were measured at 25°C. at various shear rates with a Brookfield Viscometer, Model LVF, employing a number 4 spindle with speeds of 60, 12 and 6 R.P.M.

TABLE IV

| Conc. of Polysaccharide (grams/100 mls) | Viscosity (cps) | | |
|---|---|---|---|
| | 60 r.p.m. | 12 r.p.m. | 6 r.p.m. |
| 0.2 | 180 | 250 | 450 |
| 0.5 | 750 | 2,250 | 3,900 |
| 0.8 | 1,360 | 5,750 | 10,200 |
| 1.0 | 1,950 | 7,500 | 14,200 |
| 1.3 | 2,500 | 10,600 | 20,000 |
| 1.5 | 3,500 | 13,000 | 24,900 |
| 2.0 | 5,000 | 16,500 | 34,000 |

The effect of temperature on the viscosity of aqueous solutions containing Heteropolysaccharide-7 was determined by making up a 1% by weight aqeous solution of the heteropolysaccharide and measuring its viscosity at varying temperatures ranging from 4° to 90°C. using a Brookfield Viscometer, Model LVF, employing a No. 4 spindle at 60 r.p.m. The results appear in Table V.

TABLE V

| Temperature °C. | Viscosity (cps)* |
|---|---|
| 5 | 1900 |
| 10 | 1950 |
| 15 | 2000 |
| 20 | 1950 |
| 25 | 1950 |
| 30 | 1950 |
| 40 | 1900 |
| 50 | 1900 |
| 60 | 1950 |
| 68 | 1850 |
| 79 | 2000 |
| 85 | 1850 |

*Average value from three readings.

As seen from the above table, the viscosities of an aqueous solution containing the novel heteropolysaccharide of the present invention are surprisingly stable with respect to changes in temperature. This, of course, is a highly advantageous property for end uses in which the compound is subjected to heat. An example of such an end use is the use of the novel heteropolysaccharide in a drilling fluid or as an additive to water to produce a thickened aqueous media for the recovery of oil from an underground formation by water flooding.

In still further tests, a 1% aqueous solution of Heteropolysaccharide-7 in water was heated for 15 minutes at 121°C. On cooling, it was found that the viscosity loss was only 10%, which was quite remarkable since most heteropolysaccharides are not nearly this thermally stable. A similar pattern was observed in still another test where a 1% aqueous solution of the heteropolysaccharide was maintained at a temperature of 90°± 3°C. for 60 minutes.

In still other tests, set forth in Table VI, 1% solutions of the heteropolysaccharide were made up at varying pH's in distilled water. The pH of the solution was varied by the addition of either 5.9 N hydrochloric acid or 11.7 N potassium hydroxide. The viscosity of the resulting solutions was then measured using a Brookfield Viscometer, Model LVF, using a No. 4 spindle at 60 R.P.M. and a temperature of 25°C.

TABLE VI

| pH | Viscosity |
|---|---|
| 1.12 | 1100 |
| 1.28 | 1125 |
| 1.45 | 1175 |
| 1.70 | 1400 |
| 1.85 | 1700 |
| 1.90 | 1750 |
| 2.55 | 2250 |
| 2.70 | 2250 |
| 3.55 | 2200 |
| 5.2 | 2200 |
| 6.7 | 2000 |
| 7.88 | 2100 |
| 10.70 | 2100 |
| 11.25 | 2100 |
| 11.48 | 2175 |
| 11.75 | 2350 |
| 12.0 | 2400 |
| 12.25 | 2475 |
| 12.38 | 2500 |
| 12.60 | 2600 |
| 12.80 | 500 |

As illustrated in the above table, the viscosities of aqueous solutions containing the Heteropolysaccharide-7 exhibit an outstanding stability over a very wide pH range from approximately 2.5 to 11.5. The viscosities beyond this range increase somewhat and are then followed by a sudden irreversible collapse.

In still other tests, set forth in Table VII, the effects of three monovalent, three divalent, and two trivalent salts were tested. In these tests, one solution was made up for each of the salts to be tested. The concentration of the individual salt was then sequentially increased. As the concentration was increased, the viscosity of the solution at the increased salt level was then measured using a Brookfield Viscometer, Model LVF, using a No. 4 spindle at 60 R.P.M. and a temperature of 25°C. There was a time lapse of approximately 30 minutes between each of the measured viscosities for a particular salt, as required in order to increase the concentration of the salt for the next measurement.

TABLE VII

| Concentration of salt (%) | VISCOSITY (cps) | | | | | | | |
|---|---|---|---|---|---|---|---|---|
| | NaCl | KCl | CaCl$_2$ | (NH$_4$)$_2$SO$_4$ | MgSO$_4$ | ZnSO$_4$ | Cr(NO$_3$)$_3$ | Al(NO$_3$)$_3$ |
| 0.0 | 2050 | 2050 | 2050 | 2050 | 2000 | 2000 | 2050 | 2050 |
| 0.3 | 2450 | 2400 | 2500 | 2250 | 2400 | 2450 | 2475 | 2450 |
| 0.5 | 2550 | 2425 | 2525 | 2300 | 2425 | 2425 | 2425 | 2500 |
| 1.0 | 2550 | 2500 | 2550 | 2350 | 2425 | 2425 | 2425 | 2525 |
| 1.5 | 2550 | 2500 | 2550 | 2400 | 2425 | 2450 | 2475 | 2575 |
| 2.0 | 2550 | 2450 | 2550 | 2425 | 2425 | 2450 | 2450 | 2600 |
| 2.5 | 2600 | 2500 | 2550 | 2475 | 2425 | 2450 | 2450 | 2650 |
| 3.0 | 2650 | 2475 | 2525 | 2500 | 2425 | 2450 | 2475 | 2650 |

As shown by the data in Table VII, the viscosity increased initially with all of the various salts on the addition of a small amount thereof up to about 0.3% by weight. From this point on, further additions of the salts did not increase the viscosities significantly.

In still further tests, the rheology of a 1% solution of the heteropolysaccharide of the invention in distilled water was determined over a wide shear range. This data are set forth in Table VIII in which the measured viscosity was determined with a Brookfield Viscometer, Model LVF, using a No. 3 spindle at a temperature of 25°C.

TABLE VIII

| Shear Rate (RPM) | Viscosity (CPS) |
|---|---|
| 0.3 | 144,800 |
| 0.6 | 82,500 |
| 1.5 | 42,880 |
| 3.0 | 24,800 |
| 6.0 | 13,600 |
| 12.0 | 7,300 |
| 30.0 | 3,250 |
| 60.0 | 1,900 |

As demonstrated by the above data, Heteropolysaccharide-7 of this invention is highly pseudoplastic. This is quite an advantageous property in various end uses. By way of example, in the case of a water base paint, the use of the heteropolysaccharide of the invention as a paint additive provides a paint which has a high viscosity at rest and thus does not drip or sag. However, when the paint is subjected to shear forces, as by the application of a roller or brushing, the viscosity of the paint drops markedly so that it is easily spread on the surface to which it is applied. In addition, this additive greatly improves the flow and levelling properties of the paint.

The highly pseudoplastic properties imparted by the heteropolysaccharide are also advantageous when it is added to a drilling fluid. When the fluid is at rest or near rest, it has a high viscosity and thereby suspends solids, such as drill cuttings, contained therein. However, the fluid is also readily pumped since its viscosity drops immediately when it encounters the high shear forces imparted by the pump impeller.

In still further tests as set forth in Table IX, it was found that the combination of a high pH in the order of about 10.5 to about 11.0 coupled with the use, in combination, of the polysaccharide of the invention and a water soluble salt containing a polyvalent metal cation produced a gelling of the heteropolysaccharide solution. These tests were conducted in a Brookfield Viscometer, Model LVF, at 60 R.P.M. using a No. 3 spindle at about 25°C.

TABLE IX

| | Viscosity (cps) | | |
|---|---|---|---|
| | Original | After Salt Addition | At High pH of about 10.5 to 11 |
| 0.3% by wt. of Polysaccharide-7 0.3% by wt of CrCl$_3$ | 290 | 330 | 440 (gel) |
| 0.5% by wt of Polysaccharide-7 0.2% by wt. CaCl$_2$ | 950 | 1100 | gel |
| 0.2% by wt. of Polysaccharide-7 0.1% by wt. of CaCl$_2$ | 160 | 180 | 360 (gel) |

Still other desirable properties of the heteropolysaccharide of the invention were determined by tests in which the compound was added to sea water obtained from the Bay of San Diego, Calif., and to a brine water from Permiam in Western Texas which is saturated with a mixture of salts. The heteropolysaccharide went into solution readily in both the sea water and in the salt-saturated brine water from West Texas.

The effect of polyvalent metal ions on the rheological properties of the heteropolysaccharide when dissolved in either fresh or salt water is demonstrated in Table X.

TABLE X

| Rheological readings | Before Cr+++ Addition | pH | After Cr+++ Addition | pH |
|---|---|---|---|---|
| With tap water: | | | | |
| Apparent viscosity (cps) | 10.7 | 6.9 | 40.7 | 9.0–9.5 |
| Plastic viscosity (cps) | 6.0 | | 24.0 | |
| Yield point (lb/100 ft$^2$) | 9.4 | | 33.4 | |
| With sea water: | | | | |

TABLE X-continued

| Rheological readings | Before Cr+++ Addition | pH | After Cr+++ Addition | pH |
|---|---|---|---|---|
| Apparent viscosity (cps) | 9.5 | | 16.6 | |
| Plastic viscosity (cps) | 5.0 | 7.5 | 10.6 | 9.0–9.5 |
| Yield point (lb/100 ft.²) | 9.0 | | 12.0 | |
| With brine water: | | | | |
| Apparent viscosity (cps) | 11.4 | | 19.1 | |
| Plastic viscosity (cps) | 7.0 | 6.8 | 12.8 | 9.0–9.5 |
| Yield point (lb/100 ft²) | 8.8 | | 12.6 | |

In performing the tests reported in Table X, one gram portions of the Heteropolysaccharide-7 were each dissolved in 350 ml. of water, either tap water, sea water or in saturated brine water from permiam in West Texas. Following addition of the heteropolysaccharide, the apparent viscosity, the plastic viscosity, and the yield point of the solutions were determined at about 25°C. using a Fann V-G meter, Model 135. The apparent viscosity (AV) in centipoises is measured at a shear rate of 1022 reciprocal seconds and the plastic viscosity (PV) measured in centipoises is equal to twice the apparent viscosity minus the viscosity measured at a shear rate of 511 reciprocal seconds. For Newtonian fluids, the plastic viscosity and the apparent viscosity are the same. For pseudoplastic liquids, however, the plastic viscosity is less than the apparent viscosity. The yield point (YP) of the liquid is the theoretical force necessary to shear a fluid if it behaves as a Bingham plastic and is determined from the equation (YP = 2 AV − 2 PV). The values of the yield point, as shown in Table X, are expressed in pounds per 100 square feet.

After measuring the apparent viscosity, the plastic viscosity and the yield point of the tap water, sea water and brine water containing the heteropolysaccharide, 0.3 grams of $CrCl_3 \cdot 3H_2O$ was added to each of the aqueous media after the pH thereof had been adjusted to 9.0 – 9.5. Following this, the apparent viscosity, the plastic viscosity, and the yield point of each of the media was determined with a Fan V-G meter as described above.

As shown in Table X, all of the aqueous media which contained the Heteropolysaccharide-7 were pseudoplastic since their plastic viscosities were considerably less than their apparent viscosities. Further, the data demonstrates that the presence of a polyvalent metal ion in conjunction with the heteropolysaccharide causes a significant increase in the apparent viscosity, the plastic viscosity and the yield point.

As demonstrated by all of the foregoing data, the Heteropolysaccharide-7 of this invention is very effective in thickening aqueous media to produce media having highly pseudoplastic viscosities, which viscosities are quite stable over a wide range of temperatures and a wide pH range.

In utilizing the heteropolysaccharide of the invention to thicken aqueous media, the polysaccharide is present in an effective amount to thicken the media, which amount may range from about 0.1% to about 2% by weight of the water therein. Even lower concentrations may be satisfactorily used depending on the desired result. For instance, concentrations down to 0.005% (by weight of the water therein) are effective in stabilizing foams, such as in beer.

As demonstrated by the foregoing data, Heteropolysaccharide-7 may be employed in admixture with a salt which is soluble to some degree in water and which contains a di- or trivalent metal ion. By way of example, the metal ion present in the salt may be $Cr^{+++}$, $Zn^{++}$, $Al^{+++}$, $Cu^{++}$, $Mg^{++}$, $Fe^{++}$ or $Fe^{+++}$, and $Ca^{++}$, or mixtures thereof; representative examples of the anions or mixtures thereof present in the salt are acetate; halides, such as the chloride or bromide, sulfate, or lignosulfonate. Typical examples of such salts are chromium chloride, aluminum sulfate, copper chloride, ferric chloride, zinc chloride, chromium nitrate, ferrous chloride, chromium lignosulfonate, chromium sulfate, calcium sulfate, and the like. Mixed salts and mixtures of salts may, of course, be employed. The weight ratio of the salt to the heteropolysaccharide may range from about 0.02:1 up to about 0.6:1. A thickened aqueous media containing a mixture of the salt and Heteropolysaccharide-7 will contain an effective quantity of the mixture to thicken the media which will range up to a total concentration of about 3% by weight of the water therein. The particular ratio of salt to Heteropolysaccharide-7 and the particular concentration of the mixture employed in an aqueous media may, of course, be varied depending on the desired use of the aqueous media, the particular metal ion present in the salt, the solubility of the salt in water, and the molecular weight of the salt and its effect in determining the ratio of the metallic ion with respect to the Heteropolysaccharide-7.

Our invention also includes the use of the Heteropolysaccharide-7 in combination with a di- or trivalent metal salt, which is water soluble to some degree, and whose cations are capable of cross-linking the heteropolysaccharide in an aqueous media at a pH of about 8 to about 11 to convert the aqueous media to a gel. Suitable salts which may be employed are the same as described previously for thickening an aqueous media when employed therein in combination with the heteropolysaccharide. In forming gels, it is necessary that the weight ratio of the metal-containing salt to the heteropolysaccharide be within the range of about 1:5 to about 2:1. The total concentration of the mixture in the aqueous media should, of course, be effective to form a gel at a pH of about 8 to about 11, and ranges up to about 4% by weight of the water therein. The concentration of the heteropolysaccharide in said media ranges up to about 2% by weight of the water.

In forming water base paints which contain an effective quantity, e.g., about 0.01 to about 2% by weight of the paint, of the heteropolysaccharide of the invention to thicken said paint, the paint contains an aqueous emulsion latex composition containing a resinous film forming agent and a pigment. The paint may also contain other ingredients such as extenders, anti-foaming agents, dispersion agents, freeze-thaw stabilizers and preservatives. The binder may, for example, be any of the known synthetic plastic semi-solids such as styrene-butadiene copolymers, polystyrene in both post and preplasticized systems, polyacrylate emulsions and polyvinyl acetate emulsions. The paint will contain a pigment, as stated above, which, for example, may be finely divided titanium dioxide, lithopone, zinc oxide, and the like are also used and usually in combination with extenders such as mica, talc, china clay, barium sulphate, calcium carbonate, dolomite, calcium silicate, silica, and diatomaceous earth. To such pigment, colors may be added such as organic pigments, iron oxide, chromic oxide, carbon black, sienna, umber, and ochre.

Water base paints may also include quite a variety of wetting or dispersing agents such as polyphosphates, pyrophosphates, anionic and non-ionic surfactants, polyacrylates, polymethacrylates, polyvinyl alcohol, polyethylene-glycol. Additional ingredients include freeze-thaw stabilizers such as ethylene glycol, diethylene glycol, and non-ionic surfactants; and preservatives such as organo-mercuric and organo-tin compounds, alkylated, halogenated or arylated phenols and their derivatives, antibiotics and many others. Still other ingredients may be included in water base paint formulae which are materials known as foam breakers, e.g. silicones, ditertiary acetylenic glycols, long chain ethylene oxide condensates, tributyl phosphate, pine oil, and higher aliphatic alcohols. Water base paints including the heteropolysaccharide in accordance with our invention, to impart the novel properties hereinbefore described, may also include such materials as starch, casein, methyl cellulose, hydroxy ethyl cellulose, vegetable gum, and the like.

The heteropolysaccharide of the invention may be utilized in drilling fluids, completion fluids, workover fluids and other aqueous media from which the fluid losses to subterranean strata must be controlled. In some applications, the heteropolysaccharide may be used in water or brine without other additives being present. In most instances other materials will be utilized in the media in which the polysaccharide is employed. Materials which may be present in muds and similar compositions include weighting agents such as barium sulfate, amorphous silica and calcium carbonate; gel forming materials such as bentonite and Attapulgus clay; viscosity modifying agents such as sodium metasulfate, guebracho, and calcium lignosulfonate; calcium treating agents such as lime, calcium sulfate and calcium chloride; emulsifiers such as petroleum sulfonate, tall oil soap and sodium lignosulfonate; and mixing oils such as crude oils and diesel oils. It will be understood that not all of these constituents will normally be present in any one drilling mud or other composition and that the amount of any particular material will be governed in part by the other constituents utilized and the service for which the composition is intended.

The polysaccharide may be employed as a fluid loss control agent in drilling fluids and similar compositions in an effective concentration between about 0.05% and about 3.0%, based on the dry weight of the fermentate and the weight of liquid constituents in the fluid. The concentration employed will depend in part upon the severity of the fluid loss control problem which must be overcome, in part upon the viscosity of the composition in which the fermentate is to be used, and in part upon the other constituents of the mud or other composition. Most drilling muds and similar compositions contain suspended inorganic solids which alleviate fluid loss problems to some extent and thus a lower fermentate concentration than would otherwise be required may be satisfactory.

Similarly, when the heteropolysaccharide of the present invention is used in water flooding, it is added to water to thicken it to a sufficient viscosity under normal reservoir conditions to permit effective displacement of crude oil from the reservoir to be waterflooded. The viscosity required in a particular operation will depend upon the viscosity of the crude oil contained in the reservoir, the reservoir permeability to oil, and the permeability with respect to water. These are interrelated by the mobility ratio, defined by the equation $$MR = \frac{V_o K_w}{V_w K_o}$$

where K designates the reservoir permeability, V represents viscosity, and the subscripts $w$ and $o$ denote water and oil respectively. A mobility ratio of unity indicates that the water and oil will move through the reservoir in the presence of one another with equal ease. At a mobility ratio greater than 1, displacement of oil by the water is relatively inefficient and hence the water tends to bypass oil contained in zones of low permeability. A mobility ratio less than 1 permits reasonably effective displacement of the oil by the injected water. Where practical, the viscosity of the aqueous solution should be sufficient to give a mobility ratio less than 1. It will be understood, however, that process efficiency can be improved by increasing the viscosity of the water even though the increase is not sufficient to produce a mobility ratio less than 1.

The thickened water is then pumped into the reservoir in a conventional manner. As the thickened water moves through the formation, it displaces oil therefrom and propels the oil toward one or more production wells from which the displaced crude oil is to be recovered.

Still other uses for the heteropolysaccharide of our invention is as a suspending agent in preparing aqueous titanium dioxide and/or clay, glaze suspensions, as a additive to textile print pastes, or in the formation of low drift aqueous herbicide compositions. Additional uses for our novel heteropolysaccharide are as an additive to foods in forming salad dressings, in thickening soft drink beverages, and in forming thickened puddings, and in industrial uses such as a thickener in cleaners and polishes, or as a thickener in adhesive compositions.

Although the bacteria employed in the present invention are similar in some respects to *Azotobacter inducus*, Heteropolysaccharide-7 of the present invention differs considerably from the polysaccharide produced by *A. indicus*. The polysaccharide produced by *A. indicus* is described as a polymer consisting of glucose, glucuronic acid and aldoheptose in the ratio of 3:2:1 ("Polysaccharide Produced by *Azotobacter indicus*", C. M. Quinnell, S. G. Knight and P. W. Wilson, Can J. Microbiol., Vol. 3, pg. 277, 1957), and as a linear molecule composed of repeating units of D-glucuronic acid, D-glucose and D-glycero-D-mannoheptose ("The Structure of the Extracellular Polysaccharide of *Axotobacter indicum*," V. M. Parikh and J. K. N. Jones, Can. J. Chem., Vol. 41(II), pgs. 2826–35 (1963). The heteropolysaccharides reported by Lopez et al. (Microbiol. Espan. 1968 21(1–2) p. 53) as produced by strains of Beijerinckia and Azotobacter also differ from Heteropolysaccharide-7.

What is claimed is:

1. The compound Heteropolysaccharide-7, said heteropolysaccharide having an acetyl content of about 8–10%, and the carbohydrate portion thereof consisting of about 73% glucose, about 16% rhamnose and about 11% of a uronic acid, said heteropolysaccharide being soluble in water.

\* \* \* \* \*